(12) United States Patent
Elliott et al.

(10) Patent No.: US 9,161,708 B2
(45) Date of Patent: Oct. 20, 2015

(54) GENERATION OF PERSONALIZED TRAINING REGIMENS FROM MOTION CAPTURE DATA

(71) Applicant: P3 Analytics, Inc., Santa Barbara, CA (US)

(72) Inventors: Marcus Elliott, Santa Barbara, CA (US); James Ballantyne, Santa Barbara, CA (US); Timothy Rouse, Santa Barbara, CA (US); Eric Leidersdorf, Westlake Village, CA (US)

(73) Assignee: P3 Analytics, Inc., Los Angeles, CA (US)

( * ) Notice: Subject to any disclaimer, the term of this patent is extended or adjusted under 35 U.S.C. 154(b) by 0 days.

(21) Appl. No.: 13/829,840

(22) Filed: Mar. 14, 2013

(65) Prior Publication Data

US 2014/0228712 A1 Aug. 14, 2014

Related U.S. Application Data

(60) Provisional application No. 61/765,014, filed on Feb. 14, 2013.

(51) Int. Cl.
*A61B 5/103* (2006.01)
*A61B 5/117* (2006.01)
(Continued)

(52) U.S. Cl.
CPC .............. *A61B 5/11* (2013.01); *A61B 5/1124* (2013.01); *A63B 71/06* (2013.01); *G06F 19/3481* (2013.01); *A61B 5/002* (2013.01); *A61B 5/0205* (2013.01); *A61B 5/1114* (2013.01); *A61B 5/1121* (2013.01); *A61B 5/1127* (2013.01); *A61B 5/4528* (2013.01); *A61B 2503/10* (2013.01); *A61B 2505/09* (2013.01); *A61B 2562/0219* (2013.01); *A63B 24/0003* (2013.01); *A63B 2220/89* (2013.01)

(58) Field of Classification Search
CPC ...... A61B 5/11; A61B 5/1114; A61B 5/1123; A61B 5/1124; A61B 5/1127; A61B 5/1128; A61B 5/4528; A61B 2562/0219; A61B 2505/09; A63B 24/0003; A63B 24/0009; A63B 24/0012; A63B 24/0015; A63B 2220/89
USPC ............ 600/587, 595; 463/8, 31, 37; 482/8, 9
See application file for complete search history.

(56) References Cited

U.S. PATENT DOCUMENTS 4,885,687 A 12/1989 Carey
5,984,684 A 11/1999 Brostedt et al.
(Continued)

OTHER PUBLICATIONS

"Injury prevention and performance optimization research funded by the Department of State", University of Pittsburgh, Case Study Vicon Hardware, www.vicon.com, last accessed Dec. 20, 2012.
(Continued)

*Primary Examiner* — Devin Henson
(74) *Attorney, Agent, or Firm* — Foley and Lardner LLP; John D. Lanza

(57) ABSTRACT

The use of motion capture data for analyzing an individual's performance on certain exercises, and more particularly relates to comparison of movement data for an individual with a database of recorded motions for a population in order to generate a training regimen for the individual, and to monitor the individual's progress when carrying out the training regimen.

18 Claims, 2 Drawing Sheets

(51) Int. Cl.
*A61B 5/11* (2006.01)
*A63B 71/06* (2006.01)
*G06F 19/00* (2011.01)
*A63B 24/00* (2006.01)
*A61B 5/00* (2006.01)
*A61B 5/0205* (2006.01)

(56) References Cited

U.S. PATENT DOCUMENTS

| | | | |
|---|---|---|---|
| 7,264,554 B2* | 9/2007 | Bentley | 473/222 |
| 7,946,960 B2 | 5/2011 | Vitolo et al. | |
| 7,972,245 B2 | 7/2011 | Temple et al. | |
| 7,988,647 B2* | 8/2011 | Bunn et al. | 600/595 |
| 8,103,517 B2 | 1/2012 | Hinnebusch | |
| 8,162,804 B2 | 4/2012 | Tagliabue | |
| 8,165,901 B2 | 4/2012 | Raymond | |
| 8,175,326 B2* | 5/2012 | Siegel | 382/100 |
| 8,206,266 B2 | 6/2012 | Hall | |
| 8,213,680 B2 | 7/2012 | Fitzgibbon et al. | |
| 8,224,652 B2 | 7/2012 | Wang et al. | |
| 8,306,635 B2 | 11/2012 | Pryor | |
| 8,527,217 B2* | 9/2013 | Moodie | 702/41 |
| 2002/0145563 A1 | 10/2002 | Kane et al. | |
| 2005/0013467 A1 | 1/2005 | McNitt | |
| 2006/0022833 A1 | 2/2006 | Ferguson et al. | |
| 2006/0084516 A1 | 4/2006 | Eyestone et al. | |
| 2006/0166737 A1 | 7/2006 | Bentley | |
| 2007/0270214 A1 | 11/2007 | Bentley | |
| 2008/0061949 A1 | 3/2008 | Ferguson et al. | |
| 2008/0096726 A1 | 4/2008 | Riley et al. | |
| 2008/0191864 A1 | 8/2008 | Wolfson | |
| 2009/0023555 A1 | 1/2009 | Raymond | |
| 2009/0220124 A1 | 9/2009 | Siegel | |
| 2009/0233769 A1 | 9/2009 | Pryor | |
| 2009/0300513 A1 | 12/2009 | Nims et al. | |
| 2010/0070453 A1 | 3/2010 | Yoo et al. | |
| 2010/0112533 A1 | 5/2010 | Chan et al. | |
| 2010/0144414 A1 | 6/2010 | Edis et al. | |
| 2010/0173274 A1 | 7/2010 | Hutchison | |
| 2010/0176952 A1 | 7/2010 | Bajcsy et al. | |
| 2010/0222711 A1* | 9/2010 | Lajeunesse | 600/595 |
| 2010/0279825 A1 | 11/2010 | Riley et al. | |
| 2010/0303303 A1 | 12/2010 | Shen et al. | |
| 2010/0306716 A1* | 12/2010 | Perez | 715/863 |
| 2011/0007275 A1 | 1/2011 | Yoo et al. | |
| 2011/0028800 A1 | 2/2011 | Reichow et al. | |
| 2011/0034300 A1 | 2/2011 | Hall | |
| 2011/0058709 A1 | 3/2011 | Kipman et al. | |
| 2011/0060537 A1 | 3/2011 | Moodie | |
| 2011/0112443 A1 | 5/2011 | Williams | |
| 2011/0183780 A1 | 7/2011 | Leech et al. | |
| 2011/0199393 A1 | 8/2011 | Nurse et al. | |
| 2012/0047468 A1 | 2/2012 | Santos et al. | |
| 2012/0077164 A1 | 3/2012 | Yoo et al. | |
| 2012/0092618 A1 | 4/2012 | Yoo et al. | |
| 2012/0095578 A1 | 4/2012 | Tchao et al. | |
| 2012/0122574 A1 | 5/2012 | Fitzpatrick et al. | |
| 2012/0139731 A1 | 6/2012 | Razoumov et al. | |
| 2012/0163723 A1 | 6/2012 | Balan et al. | |
| 2012/0169491 A1 | 7/2012 | Chang et al. | |
| 2012/0178534 A1 | 7/2012 | Ferguson et al. | |
| 2012/0179278 A1 | 7/2012 | Riley et al. | |
| 2012/0253201 A1* | 10/2012 | Reinhold | 600/473 |
| 2012/0277635 A1* | 11/2012 | Tsai et al. | 600/595 |
| 2013/0123667 A1* | 5/2013 | Komatireddy et al. | 600/595 |
| 2013/0190135 A1 | 7/2013 | Pryor | |

OTHER PUBLICATIONS

Ferber, "Vicon Motion Capture Helps the Running Injury Clinic Investigate and Prevent Athlete Injury", University of Calgary, Running Injury Clinic, 2011, www.vicon.com.

Ren, et al., "Learning Silhouette Features for Control of Human Motion", ACM Transactions on Graphics, vol. 24, No. 4, Oct. 2005, pp. 1303-1331.

Liu, et al., "A System for Analyzing and Indexing Human-Motion Databases", SIGMOD, Jun. 2005, pp. 1-3.

Guerra-Filho, et al., "The human motion database: A cognitive and parametric sampling of human motion", Image and Vision Computing, vol. 30, Issue 3, Mar. 2012, pp. 251-261 (Abstract only attached from www.sciencedirect.com).

"Gait analysis: an objective method for the analysis of walking patterns", Qualisys Motion Capture Systems, Qualisys AB, 2008, www.qualisys.com.

Liu, et al., "Realtime Human Motion Control with a Small Number of Inertial Sensors", Association for Computing Machinery, Inc. (ACM), Feb. 2011, San Francisco, CA, pp. 133-140.

Garofalo, "Healthcare Applications Based on MEMS Technology", Advancing Microelectronics, Mar./Apr. 2012, vol. 39, No. 2, pp. 24-28.

Kuehne, et al., "HMDB: A Large Video Database for Human Motion Recognition", ICCV, 2011.

Keogh, et al., "Indexing Large Human-Motion Databases", Proceedings of the 30th VLDB Conference, Toronto, Canada, 2004, pp. 780-791.

Yamane, et al., "Human Motion Database with a Binary Tree and Node Transition Graphs", Auton Robot, 2011, vol. 30, pp. 87-98.

Guerra-Filho, et al., "A Human Motion Database: The Cognitive and Parametric Sampling of Human Motion", Department of Computer Science and Engineering, University of Texas at Arlington, http://smile.uta.edu/hmd/, accessed Aug. 20, 2013.

"Microsoft Xbox 360 Kinect—Your Shape Fitness Evolved (FULL E3 video)", http://www.youtube.com/watch?v=N0_4YEx07rw, web site accessed Aug. 20, 2013.

"Carnegie Mellon Graphics Lab: Motion Capture and File Formats", http://www.mocap.cs.cmu.edu/info.php, web site accessed Aug. 20, 2013.

"How It Works: IKKOS Training", http://www.ikkos.com/how-ikkos-works/, web site accessed Aug. 20, 2013.

"How Kinect depth sensor works—stereo triangulation?", Mirror Image, http://www.mirror2image.wordpress.com/2010/11/30/how-kinect-works-stereo-triangulation/, web site accessed Aug. 20, 2013.

"Inertial Measurement of Human Walking", Human Biomechanics and Control Lab: Current Interests, 2007, http://www.personal.umich.edu/~artkuo/Lab/2008/07/inertial-measurement-of-human-walking.html, web site accessed Aug. 20, 2013.

"The natural motion of the human body is captured and analyzed without attaching markers or straps", Stanford University: BioMotion Laboratory Mechanical Engineering, http://www.stanford.edu/group/biomotion/markerless2011.html, web site accessed Aug. 20, 2013.

"Kinect", Wikipedia, http://www.en.wikipedia.org/wiki/Kinect, web site accessed Aug. 20, 2013.

Schramm, "Kinect: The company behind the tech explains how it works", Joystiq, Jun. 19, 2010, http://www.joystiq.com/2010/06/19/kinect-how-it-works-from-the-company-behind-the-tech/, web site accessed Aug. 20, 2013.

Zheng, "Microsoft Research reveals guts of Kinect technology", istartedsomething, Mar. 19, 2011, http://www.istartedsomething.com/20110319/microsoft-research-reveals-guts-of-kinect-technology/, web site accessed Aug. 20, 2013.

"Motion Capture Systems", http://www.personal.umich.edu/~kzelik/Motion_Capture_Systems.html, web site accessed Aug. 20, 2013.

"Nike+Kinect Training—Xbox.com", http://www.xbox.com/en-US/marketplace/product/nike-kinect-training, web site accessed Aug. 20, 2013.

"Optical Motion Capture Systems", Mocap Resources, http://www.metamotion.com/motion-capture/optical-motion-capture-1.htm, web site accessed Aug. 20, 2013.

"OptiTrack—ARENA Downloads—Software, motion capture data (BVH, C3D and FBX) and more", http://www.naturalpoint.com/optitrack/downloads/arena.html#sampleData, web site accessed Aug. 20, 2013.

(56) References Cited

OTHER PUBLICATIONS

"Our System", Jintronix, 2013, http://www.jintronix.com/our-system/.

Fanelli, et al., "Random Forests for Real Time Head Pose Estimation", http://www.vision.ee.ethz.ch/~gfanelli/head_pose/head_forest.html, web site accessed Aug. 20, 2013.

"Xsens MVN—Inertial Motion Capture", XSENS, http://www.xsens.com/en/general/mvn?gclid=CODAqZzXI7ECFaMaQgodIEHnCQ, web site accessed Aug. 20, 2013.

Non-Final Office Action mailed on Sep. 30, 2014 in U.S. Appl. No. 14/181,554, filed Feb. 14, 2014.

* cited by examiner

GENERATION OF PERSONALIZED TRAINING REGIMENS FROM MOTION CAPTURE DATA

CLAIM OF PRIORITY

This application claims the benefit of priority under 35 U.S.C. §119(e) to U.S. provisional application Ser. No. 61/765,014, filed Feb. 14, 2013, which is incorporated herein by reference in its entirety.

TECHNICAL FIELD

The technology described herein generally relates to use of recorded motion capture data for analyzing an individual's performance on, and specific biomechanics of, certain movements. The technology more particularly relates to comparison of movement data for an individual with a database of recorded motions for a population in order to identify movement pathologies and generate a specific training regimen for the individual to improve performance and/or reduce risk of injury, as well as to track the individual's progress.

BACKGROUND

Motion capture technologies have improved in recent years so that it is now possible for a computer to recognize the human form and to recognize and record a person's motion in three dimensions, as well as identify and track other objects in a person's environment. See, for example, www.primesense.com/solutions/technology/.

Sports medicine has for long been interested in developing metrics to facilitate diagnosis and treatment of motion-related disorders and impediments.

There has been a growing use of motion capture technology in medicine, though mostly this has been in a clinic, laboratory, or hospital setting, and in conjunction with assessment by a physician. For example, Jintronix uses motion capture to record a patient's movements in physical rehabilitation and relay them to a healthcare provider to provide for ongoing monitoring. See, e.g., www.jintronix.com/our-system/. West Health Institute has developed a product, Rehabilitation Management Tool, that allows a physical therapy patient to utilize Microsoft's Kinect to monitor whether exercises are being performed correctly. See, e.g., www.westhealth.org/institute/our-innovations/reflexion.

Motion capture technology has also been used in training and performance measurement in a sports setting. For example, Ikkos Training provides an application for allowing an athlete in training to replicate the movements of a professional. Information about the athlete's performance can also be viewed by medical personnel. See, e.g., U.S. Patent Application Publication No. US2010-0173274. In another example, Ubisoft uses Microsoft's Kinect product (e.g., www.xbox.com/en-US/KINECT) to assist an individual in practicing a work-out regime: see, e.g., www.youtube.com/watch?v=N0_4YEx07rw. Vicon uses optical marker data to monitor and analyse movements of athletes in a laboratory setting in order to quantify injuries or identify potential injuries. See, e.g., www.vicon.com/applications/life_sciences.html. Qualisys also uses motion capture based on optical tracking to monitor and analyse movements of athletes in a laboratory setting. See, e.g., www.qualisys.com/applications/biomechanics/gait-analysis-and-rehabilitation/. However, none of these technologies are used to direct training programs.

Nike has used motion capture technology in the generation of performance metrics, such as speed and endurance, but does not utilize a biomechanical analysis and does not assist an individual in identifying and improving upon movement pathologies. See, for example, nikeplus.nike.com/plus/support#answers/detail/article/nkt-settings, and: www.nike.com/us/en_us/c/training/nike-plus-kinect-training.

In sum, a way of monitoring an individual's biomechanics with motion capture technology in conjunction with providing to that individual suggested improved training regimens, outside the clinic, for example from within the comfort of the individual's home, has yet to be disclosed.

The discussion of the background herein is included to explain the context of the technology. This is not to be taken as an admission that any of the material referred to was published, known, or part of the common general knowledge as at the priority date of any of the claims found appended hereto.

Throughout the description and claims of the application the word "comprise" and variations thereof, such as "comprising" and "comprises", is not intended to exclude other additives, components, integers or steps.

SUMMARY

The technology herein includes a computer-based method for identifying a training or treatment regimen for a subject, the method being performed on at least one computer, the computer having a processor, a memory, and input/output capability. The method comprises: recording one or more exercises performed by the subject, wherein each exercise of the one or more exercises comprises three-dimensional (x,y,z)-coordinates of one or more nodes on the subject's body at a sequence of times, t, and wherein each node is selected from the group consisting of: left and right elbow, left and right wrist, left and right hand, left and right shoulder, left and right knee, left and right ankle, left and right hip, head, neck, center of hips, center of shoulders, left and right foot, and lower-back; constructing, by a first computer, a motion profile for the subject based on the one or more recorded exercises of the subject, wherein the motion profile comprises ranges of joint angle value and/or displacement experienced for one or more exercises, and/or times for various displacements; comparing, by the computer, the motion profile of the subject with a database of previously recorded motion profiles for a population of individuals; identifying a movement pathology displayed by the subject, or for which the subject is susceptible, based on a deviation between a motion profile for the subject and a statistical sampling of motion profiles for the population of individuals, or based on a prior understanding of injury and performance characteristics; and communicating, via an output device, a training regimen for the subject which alleviates one or more movement pathologies, wherein the training regimen comprises one or more exercises.

The present disclosure additionally includes an apparatus for carrying out the aforementioned method.

BRIEF DESCRIPTION OF THE DRAWINGS

Like reference symbols in the various drawings indicate like elements.

DETAILED DESCRIPTION

Definitions

Figure 1:
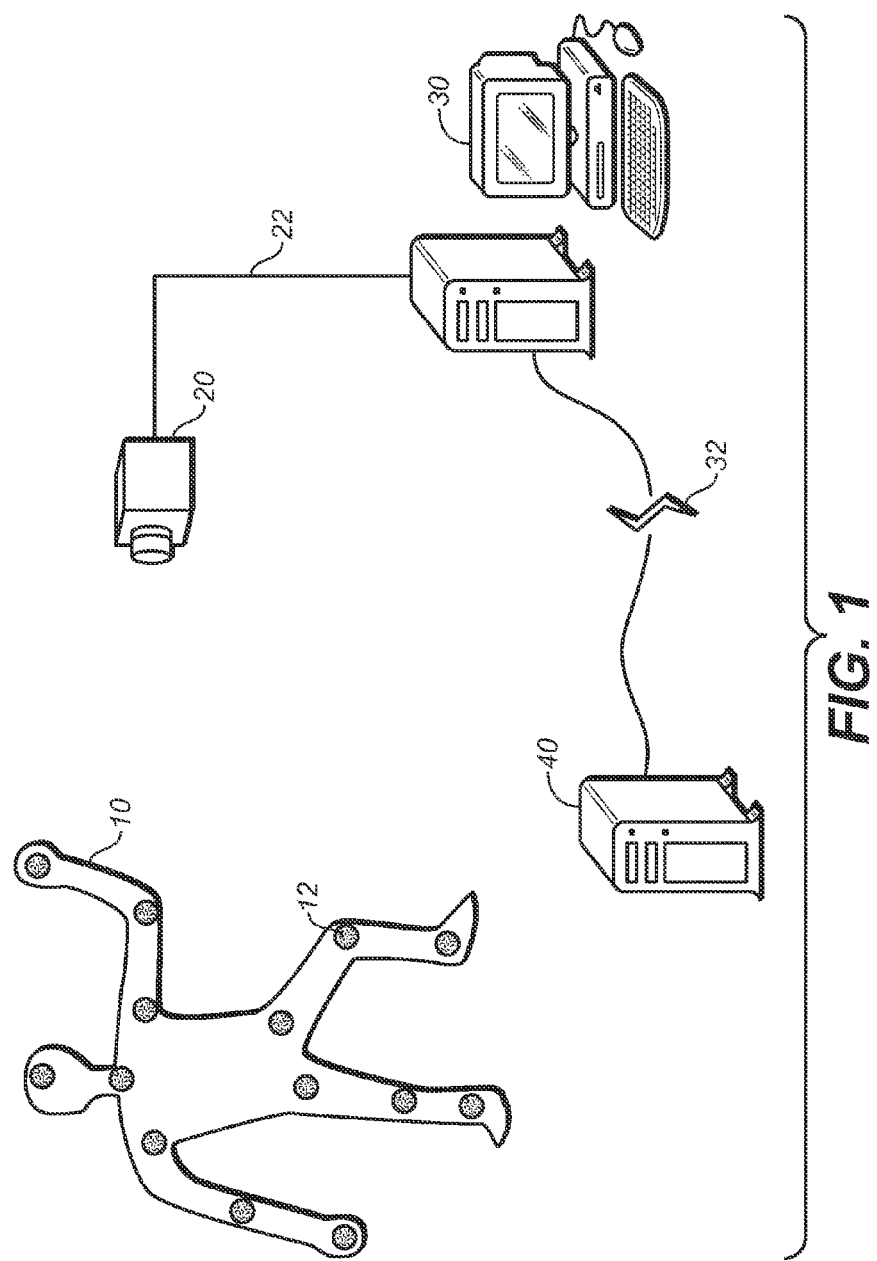
FIG. 1 shows a flow-chart of a process as described herein.

The following are various terms that may be used herein and that pertain to aspects of biomechanics.

Balance is an individual's awareness or perception of one's body in space. The ability to remain upright with proper hip/trunk positioning and minimal compensation from the upper extremities while standing on one foot, or both feet.

Body composition generally refers to the make-up of the body, considering fat content as a percentage of total body weight (among other things). There is often a high correlation between poor body composition and poor work capacity.

Dorsiflexion is a measure of ankle mobility. In particular, dorsiflexion is the ability to set the ankle joint in a flexed position—with toes up towards the shin.

Eccentric adaptation is the ability to utilize the stretch-shortening cycle of muscles, as well as the ability to utilize stretch and recoil properties inherent in tendon and muscle to enhance force applied across various joints. Eccentric adaptation includes the strength of the muscle while being stretched.

Lower Body Power is a subject's ability to generate maximal force from his or her lower extremities in a very short amount of time.

Hip stability is the maintenance of hip position throughout dynamic movement and safely transfer force from the lower extremities to the trunk.

Mobility refers to range of movement (flexion, extension, rotation, etc.) across a specific joint. For example, hip mobility is the ability to pass force through the hip musculature in a wide range of motion. This pertains to movement in all planes.

Lumbar lordosis refers to the maintenance of the natural curvature of the lumbar spine. Correct lumbar lordosis assists in generation of lower body power while maintaining the integrity of spinal disks.

Trunk stability is the ability to maintain appropriate trunk positioning during explosive movement. Deficiencies in trunk stability severely limit power generated from the lower extremities, particularly during change of direction.

Thoracic mobility—the ability to generate adequate general joint motion and extension, in particular with respect to the thoracic spine which results in an upright posture in the mid-back during athletic movements. Poor thoracic mobility can lead to increased injury risk in surrounding joints.

Thoracic rotation is the ability to rotate axially through the thoracic spine.

Varus or valgus deformations refer to the position of the knee. People with varus deformations appear bowlegged, while valgus deformations appear knock-kneed. These traits can leave an individual prone to injury. The ability (or inability) to avoid excessive varus or valgus deformations is often indicative of hip stability.

Work Capacity is the ability to maintain high level of intensity over a duration of time.

Overview

The technology described herein is designed to utilize motion capture data for a subject (an individual). The subject may be, for example, an athlete desiring specific guidance on improvement of form, or may be a patient undergoing rehabilitation. More generally, the subject may be a patient undergoing a general health and wellness check-up, or one who is being evaluated for suitability for a job or task. The subject may therefore be someone without a diagnosed condition but who is seeking information about potential vulnerabilities.

There are various techniques for recording an individual's motions in a manner that is susceptible to further analysis on a suitably programmed computer. Those techniques include but are not limited to: infra-red based methods; use of active markers; X-ray based; optical-based (e.g., www.metamotion.com/motion-capture/optical-motion-capture-1.htm); video-based (see, e.g., www.stanford.edu/group/biomotion/markerless2011.html); and inertial-based measurement units (see, e.g., www-personal.umich.edu/~kzelik/Inertial_Measurement_Units.html, www-personal.umich.edu/~artkuo/Lab/2008/07/inertial-measurement-of-human-walking.html and www.xsens.com/en/movement-science/). Video-based methods can be based on 1 or 2 cameras, as well as arrays of larger numbers of cameras, such as 4, 6, 8, 10, or 12 cameras.

The technology herein utilizes any form of motion capture technology, or combinations of different types of motion capture technology, that can provide the positions in space, at sequences of times, of various points on a subject's anatomy. Preferably the motion capture technology can be deployed in a non-laboratory setting, such as a subject's home, or at a gym, or a work-out or exercise center. It can also be applied when a subject is in a suitably equipped exercise center when travelling, such as in a hotel, or on a boat. The technology can also be applied in a physical therapy setting, for example, in monitoring a subject's progress in recovering from an injury. The technology can still further be deployed by chiropractors, for example to identify spinal or alignment abnormalities in a subject undergoing treatment.

In general, motion capture technology collects biomechanical data relating to movements of a subject through a physical space such as an exercise room, and stores the recorded movements into digital form, such as on a computer-readable medium present either locally, or accessible remotely via the Internet or other computer network.

In one embodiment, the movements performed by the subject are captured by sensors that measure the elapsed time for invisible infrared lights to be transmitted from the sensors, deflect off points on the subject's body and return to the origin. This time-based data allows the computer to calculate the distance between points on the subject's body and the sensors and, in turn, create a 3D reconstruction of the subject's movements. This technology therefore enables a computer to save and reconstruct the observed movements of the subject through the physical space.

The technology described herein utilizes motion capture technology to ascertain the biomechanical and physiological profiles of an individual such as an athlete and, following assessment, to use the information as the basis for prescribing training or treatment regimens comprising one or more exercises that reduce the risk of injury and improve athletic performance, as well as track the individual's progress as they repeat the exercises over time.

A preferred form of motion capture technology is infrared motion capture (IMC). In recent years, IMC technology has been made readily available to the general population through home gaming software, such as Kinect, by Microsoft Corporation. As the use of Kinect has largely been for gaming purposes, applications of this system for biomechanical analysis remain unfulfilled.

The performance of any athletic movement, whether a common testing procedure, such as a vertical jump, or a highly complex movement, such as a baseball pitch, may be investigated by using motion capture technology and its biomechanical variables quantified.

Initially, subjects carry out a selection of exercises to assess their biomechanical structure, whether any current injuries are apparent, and their likelihood for future injury if any deficiencies remain untreated. These exercises involve the subjects performing various movements, of the subject's full body or specific portions of the body, that challenge specific joints, muscles and systems of the body. Each exercise performed is viewed using the IMC technology, which reconstructs a 3-dimensional (3-D) image of the subject performing the test. Using the 3D reconstruction, the computer is able to measure the size of various joint angles, monitor the stability of the subject and calculate other parameters such as the ground reaction forces exhibited by the subject while performing the exercise. These derived parameters comprise a motion profile for a given exercise for that subject. The results are then processed by a suitably programmed computer, and compared to databases of motion profiles for a population to ascertain whether any movement pathologies are present. It is then possible to predict the subject's current risk of suffering specific injuries in the future. The computer is then able to develop and offer a training regimen that comprises an exercise program that will not only improve overall athleticism, but will also correct any observed movement pathologies, and thereby reduce the subject's risk of suffering future injury. The training regimen for the subject can also address potential pathologies "downstream" of an identified pathology, based on an understanding of the complex relationship between anatomical segments involved in human movement. By downstream is meant a motion in one part of the body that is adversely affected, after a limitation in motion of another part of the body has occurred. For example, as described elsewhere herein, limitations in dorsiflexion can lead to other movement pathologies at parts of a subject's anatomy remote from the foot region. Then, the subject's progress over time can be monitored by, for example, monitoring the subject as they re-perform the exercises at particular intervals.

The technology herein can be further used when deciding matters of insurance coverage. For example, by generating a risk profile for an individual, specifically tailored insurance plans can be identified or suggested.

Apparatus

Exemplary apparatus for carrying out the technology herein is shown in FIG. 1. A subject 10 performs an exercise in front of a motion capture device 20. The motion capture device 20 recognizes nodes 12 at various positions on the subject's anatomy. Shown in FIG. 1 are exemplary nodes located on the subject's body and limbs, typically at joints such as hips, knees, elbows, ankles, neck, and wrists. In some embodiments, markers can be placed at the nodes and are identified, as applicable, by the motion capture device 20. The subject is positioned so that he or she is situated in the field of view of device 20 so that the spatial positions of the nodes can be measured, as the subject carries out a motion. In still further embodiments, the apparatus can record audio data as well as motion-capture data. Audio data can include sounds made by the subject, for example, in response to certain extremes of motion that cause pain or discomfort. Recording sounds in conjunction with spatio-temporal data can provide additional data on aspects of a subject's range of motion that may be inhibited by some movement pathology.

Motion capture device 20 is connected via a communication link, such as a computer network connection, to one or more computing devices 30. The communication link can be wireless, such as by WiFi, or a short-range connection such as BlueTooth. A computing device 30 receives motion capture data from device 20, wherein the data comprises at least, (x,y,z) coordinates of the various nodes at a series of times, t. A computing device 30 may be situated in the same room as subject 10, or may be in close proximity, such as in an adjoining room of the same building. A computing device 30 has a processor and memory, and may also be equipped with user interface elements such as a display screen, keyboard, touch-sensitive display, and mouse. The computing device 30, or one or more such devices, calculates a motion profile from the motion capture data recorded for the exercises performed by the subject.

Computing device 30 is preferably connected to a remote computer 40 via another network connection 32, either wired or wireless. Remote computer 40 stores, or is separately connected to, a database containing motion profiles for a population of individuals performing various exercises. Computing device 30 communicates the motion profile recorded for subject 10 to remote computer 40, which then performs comparisons between the motion profile recorded for subject 10 and the motion profiles of the population of individuals, or to motion profiles from specific sub-populations of individuals based on specific criteria for the subject. Computer 40 may additionally add the motion profile recorded for subject 10 to the motion profiles in the database, thereby augmenting the data available. Computer 40 further identifies, based on the comparisons between the data recorded for subject 10 and the population data, one or more exercises, selected from a second database of exercises. A training regimen is constructed based on permutations of the on the one or more exercises. The training regimen is communicated via link 32 to computer 30 and displayed on an output device, and is thereby presented to subject 10, or to another interested individual such as a physician, trainer, chiropractor, or physiotherapist.

Figure 2:
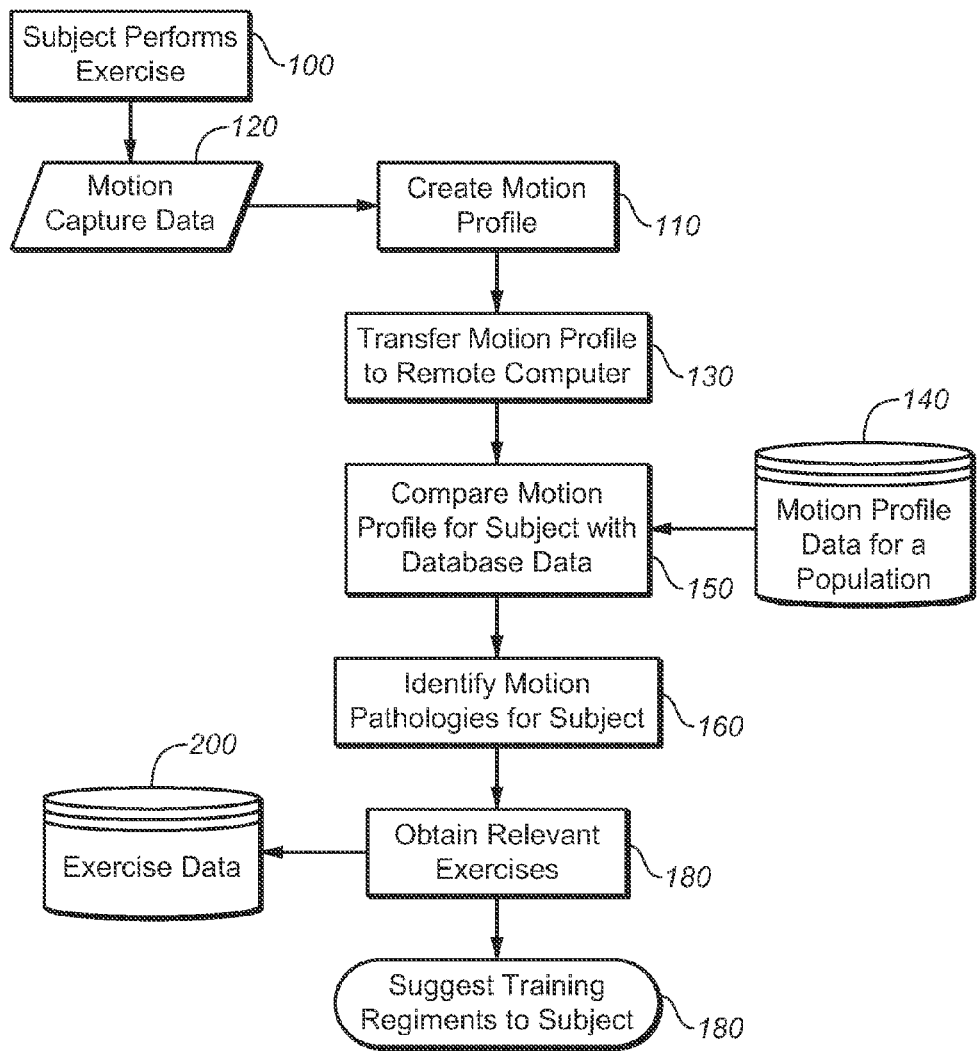
FIG. 2 shows an apparatus for performing a process as described herein.

FIG. 2 shows a flow-chart outlining an exemplary method of suggesting training regimens to a subject. In the context of rehabilitative care, such as physical therapy, a training regimen may be substituted by a treatment protocol, wherein a treatment protocol comprises one or more exercises designed to alleviate particular symptoms and facilitate the subject's recovery from an injury. A subject performs an exercise 100, within range of a motion capture device. The motion capture device collects motion capture data 120 and transmits it to a computing device that creates one or more motion profiles 110 for the subject. The one or more motion profiles are transferred 130 to a remote computer, which compares 150 the one or more motion profiles of the subject with respective motion profiles for a population of individuals stored in a database 140. From those comparisons, movement pathologies of the subject are identified 160, and are used to obtain relevant exercises 180, selected from a second database of exercise data 200. Finally, the training regimens, comprising one or more sequences of the relevant exercises, are suggested 190 to the subject, or to the subject's physician, physiotherapist, or trainer. The training regimens can be designed to rehabilitate faulty mechanics that have caused an injury, to improve diagnosed mechanical faults or structure of the subject, to reduce risk of future injury, or simply to improve the performance and function of the subject, for instance as in an athlete. Optionally, other data can be presented as well as or instead of training regimens. For example, the subject could be provided with statistical data showing how they compare to the population in the database in respect of one or more exercises.

Various implementations of the technology herein can be contemplated, particularly as performed on computing apparatuses of varying complexity, including, without limitation, workstations, PC's, laptops, notebooks, tablets, netbooks, and other mobile computing devices, including cell-phones, mobile phones, and personal digital assistants. The computing devices can have suitably configured processors, including, without limitation, graphics processors and math coprocessors, for running software that carries out the methods herein. In addition, certain computing functions are typically distributed across more than one computer so that, for example, one computer accepts input and instructions, and a second or additional computers receive the instructions via a network connection and carry out the processing at a remote location, and optionally communicate results or output back to the first computer.

The computer functions for comparing a subject's motion profile(s) with those in a database can be developed by a programmer skilled in the art. The functions can be implemented in a number and variety of programming languages, including, in some cases mixed implementations. For example, the functions as well as scripting functions can be programmed in C, C++, Java, Python, VisualBasic, Perl, .Net languages such as C#, and other equivalent languages not listed herein. The capability of the technology is not limited by or dependent on the underlying programming language used for implementation or control of access to the basic functions.

The technology herein can be developed to run with any of the well-known computer operating systems in use today, as well as others, not listed herein. Those operating systems include, but are not limited to: Windows (including variants such as Windows XP, Windows95, Windows2000, Windows Vista, Windows 7, and Windows 8, available from Microsoft Corporation); Apple iOS (including variants such as iOS3, iOS4, iOS5, and iOS6 and intervening updates to the same); Apple Macintosh operating systems such as OS9, OS 10.x (including but not limited to variants known as "Leopard", "Snow Leopard", "Lion", and "Mountain Lion"); the UNIX operating system (e.g., Berkeley Standard version); and the Linux operating system (e.g., available from Red Hat Computing); and the Android family of operating systems, as available on various cellular telephones and tablet computers.

To the extent that a given implementation relies on other software components, already implemented, such as functions for basic mathematical operations, etc., those functions can be assumed to be accessible to a programmer skilled in the art.

Furthermore, it is to be understood that the executable instructions that cause a suitably-programmed computer to execute methods for manipulating a biomechanical motion profile, as described herein, can be stored and delivered in any appropriate computer-readable format. This can include, but is not limited to, a portable readable drive, such as a large capacity "hard-drive", or a "pen-drive", such as connects to a computer's USB port, and an internal drive to a computer, and a CD-Rom or an optical disk. It is further to be understood that while the executable instructions can be stored on a portable computer-readable medium and delivered in such tangible form to a purchaser or end-user, the executable instructions can also be downloaded from a remote location to the user's computer, such as via an Internet connection which itself may rely in part on a wireless technology such as WiFi. Such an aspect of the technology does not imply that the executable instructions take the form of a signal or other non-tangible embodiment. The executable instructions may also be executed as part of a "virtual machine" implementation.

Biomechanical Screening

The motion capture technology utilized herein recognizes various points on a human's anatomy. These points, also referred to herein as nodes, correspond to joints as well as other locations that are important to a biomechanical assessment of an individual's motions. Typically, the nodes recognized include, but are not limited to, 21 locations as follows: left and right elbow, left and right wrist, left and right hand, left and right shoulder, left and right knee, left and right ankle, left and right hip, head, neck, center of hips, center of shoulders, left and right foot, and lower-back. That is, some nodes are located at joints (e.g., knees, elbows, wrists); some nodes are located elsewhere (such as center or top of head). Nodes at other locations not listed can also be measured, consistent with the technology herein. The technology herein is not limited to the number or position of node locations. The technology can be readily adapted to work with other numbers of nodes, as well as nodes at a different set of positions (e.g., including points on a subject's torso).

As an individual moves within range of the motion capture device, the positions of the nodes in 3-D space are recorded. Typically, the individual will perform an exercise that can lead to an assessment of possible movement pathologies, i.e., biomechanical deficiencies in the individual's range of movement of a particular limb or joint. The individual may also perform a number of exercises, in sequence, where each exercise tests a particular potential movement pathology.

Audio data can also be optionally recorded to monitor the subject's experience of pain or discomfort, during motion. Still other sensory data can be integrated with motion capture data to augment the data considered. Such sensory data can include, but is not limited to, measurements of respiration rate, EKG, blood oxygen content, such as from a pulse oximeter, and velocity data, such as from an accelerometer.

In preferred embodiments, coordinate data (positions in space at a series of times) for all nodes on the subject are provided and analyzed. In some embodiments, coordinate data for subsets of nodes are analyzed. For example, a subject may only require or request assistance with evaluating upper body movements, in which case only the coordinates of upper body nodes, and nodes on the arms are analyzed.

The motion capture device is connected to a first computer that records one or more exercises performed by the individual, wherein the stored form of each exercise of the one or more exercises comprises three-dimensional (x,y,z) coordinates of one or more nodes at a sequence of times, t. The length of time, t, may vary according to the particular motion being studied, but is typically from 30 seconds to a time between 1 and 2 minutes. Sampling rates may vary from one motion capture technique to another, but 30 frames per second is typical. Other sampling rates include 6, 10, 18, 24, 36, 48 and 60 frames per second.

The first computer may be in the same room as the individual performing the exercise, or may be remote from the individual but connected via a network connection (e.g., wirelessly) to the motion capture device so that it accepts and stores the movement data for the individual via wireless link.

The first computer is programmed to construct a motion profile for the individual based on the one or more recorded exercises performed by the individual. A motion profile comprises data such as ranges of joint angle value or displacement experienced for one or more of the exercises. Joint angles can be calculated from data on various nodes. For example, there is an angle at the knee joint that can be computed from knowing the positions of nodes situated at the knee, ankle and hip on the same side of the individual. The angle at the knee joint will vary through time as the individual performs an exercise such as one involving flexing of the knee. The motion profile can be stored as the maximum and minimum value of the angle while the exercise is performed. For a given assessment, it may only be necessary to process a small number of joint positions. For example, for a squat position, a critical angle is the angle between the hip, knee, and ankle. The adduction angle (knee-hip-horizontal) in this position can also be measured. Displacements, if measured, can usefully provide measures of acceleration, for example, as a person jumps.

The data that comprise a motion profile will vary from one exercise to another, depending on which nodes are in motion. However, the general form may include a sequence of (x,y,z) coordinates at time intervals, t, for a selection of nodes, as well as ranges of particular angles and/or displacements. The data can optionally be presented on a computer display, in real-time, while a subject is performing an exercise. Thus, particular ranges of joint angles are instantly available for review.

The motion profile of the individual can then be compared with a database of previously recorded motion profiles for a population of individuals. The database preferably contains data from a wide range of individuals and may include elite athletes, and older persons, as well as those with physical disabilities. Therefore, the sets of data for an individual can be compared to sub-populations of individuals of similar demographics, such as gender, age, activity level, as well as to the entire population. The database contains a set of normalized data for each exercise, and for each range of joint motion, including but not limited to maximum and minimum values of angles through movements, average values and the standard deviation of data from that average. For example, ankle flexibility (dorsiflexion) can be expressed as a pair of angles representing maximum and minimum angles attainable. The population data in the database is continually updated, as more data on a greater variety of persons is collected. The data in the database can also be based on literature from the medical community, i.e., drawing on data from past studies rather than relying exclusively on newly-made measurements.

The data accumulated in the database can form the basis of a number of different types of analysis. For particular subjects, it can be combined with other biomedical data, such as from other medical records for a patient, to provide additional insights. It is also possible to use the data to monitor how subjects' motions within a population change over time as a result of aging, and how changes over time correlate with development of certain diseases such as arthritis or neuromuscular conditions.

The comparisons can be performed by the first computer, or can be performed by a second computer, remote from the individual's exercise location. If performed by the first computer, the database may be stored on the first computer or may be stored on a second computer and accessed via a network connection. If the comparisons are performed by the second computer, the motion profile of the individual is communicated to the second computer via a network connection, such as wirelessly.

Comparisons can be performed according to various metrics. Comparisons can be made between the motion profile of the individual and an average over the motion profiles of all individuals in the database. Comparisons can be made between the motion profile of the individual and an average of motion profiles just for comparable individuals in the database, according to some demographic. For example, comparisons can be made based on gender, body mass index, activity level, and age, or combinations of two or more of those factors as filters. Typically, comparisons are based on statistical measures such as mean, variance, and standard deviation.

In some embodiments, the data for the population of individuals is fit to a standard curve, such as by polynomial regression, thereby permitting the data for a subject to be scored. Scores outside of a particular range are indicative of actual or potential movement pathologies for a given subject.

In these exemplary embodiments, the equations take the form of a polynomial regression in which subjects are graded on each biomechanical pathology for a final score out of 100. In the equations generated by this approach, "Y" denotes the score for a particular biomechanical aspect of movement; "x" can be either an average angle, standard deviation measure, time, height, or distance depending on the particular test.

An exemplary equation for dorsiflexion is: $Y=MIN(-0.0881*(x^2)+(9.5595*x)-157.14, 100)$, where x is the angle made from the knee to the ankle to the horizontal. It would be understood by one of skill in the art that the actual form of the equation depends on many factors, including characteristics of the population in the database, the units of measurement utilized, and the polynomial form. Therefore, precise coefficients of equations herein can be considered exemplary.

For many performance metrics, it is possible to establish different equations for male and female subjects. For example, for the vertical jump metric, using polynomial regression, an exemplary equation for males is: $Y=-0.1376*(x^2)+(10.573*x)-100.84$, and an exemplary equation for females is: $Y=-0.1376*(x^2)+(8.6458*x)-33.571$. In these equations, x is the vertical height attained in a given jump, and Y is the score.

For stability measures (such as hip and trunk stability) the principal factor is an average value of angles through a movement, and the standard deviation of angles from that average, as measured in each frame. The average angles provide information about a subject's biomechanical alignment, and the standard deviation from that average informs about their ability to maintain this average. Subjects can be graded on whether or not the average angle falls within a dedicated "norm", and on the amount of deviation (the smaller the better) for stability movements.

For mobility measures (such as thoracic rotation, thoracic extension, dorsiflexion) and performance measures (such as double jump, standing vertical, skater tests), the key parameters are numerical values of angles reached at the end range of motion, or times taken to perform a particular motion, distances covered, and heights. Norms can be established using a working knowledge of biomechanics, in addition to data already collected. Based on a comparison of the individual's motion profile and those profiles in the database as well as on studies from published literature and a working knowledge of biomechanics that can be introduced into the system, it is possible to ascertain if any aspect of the individual's motion profile deviates significantly from average or normal motion profiles. Statistical measures such as variance and standard deviation of the range of values of the parameters in the motion profiles stored in the database can provide guidelines of significance.

It is thereby possible to identify a movement pathology displayed by the subject, or for which the subject is susceptible, based on a significant deviation between a motion profile for the subject and a statistical sampling of motion profiles for the population of individuals. A movement pathology can be taken to include, for example, a restricted range of motion, or an inefficient combination of motions exhibited by the individual. Movement pathologies can also be identified by correlating specific movements with specific injuries subsequently sustained by individuals, as recorded in the database. Conversely, if a subject is already known to have sustained a particular injury, the system can monitor the subject's rate of progress of recovery and can assess the severity of the injury, for example, by comparison with other subjects' data at equivalent time points in the healing process.

Common movement pathologies include, but are not restricted to, limitations in ranges of motion for the following biomechanical movements: ankle dorsiflexion, inversion and eversion, hip stability, hip mobility, trunk stability, thoracic mobility, thoracic rotation, lumbar lordosis, kyphosis, varus, valgus, flexion, extension, rotation, abduction, and adduction.

Based on an identified movement pathology, it is possible to communicate to the individual, via an output device, a training regimen for the subject which alleviates the movement pathology, or a treatment regimen in the context of physical therapy. The training regimen comprises exercises selected from a database of such exercises, and is chosen based on an indexing of those exercises according to particular movement pathologies. For example, for a given joint there will be a list of appropriate exercises for the subject to perform. The database of exercises may be stored separately from the database of motion profiles. The exercises may be stored in a separate database on the same computer that stores the motion profiles, or may be stored on a different computer entirely. If stored on a different computer, it can be accessed by, e.g., a network connection between the two computers. In some embodiments, the training regimen offered to a subject comprises exercises that are algorithmically selected based on the needs that have been identified from the subject's assessment. By choosing exercises from a range of exercises, it is possible to create a fresh training regimen for each workout. The exercises can be selected automatically from a stored list of such exercises, each of which is associated with one or more movement pathologies.

It is also possible to achieve assessment customizations. It is necessary to take data from existing assessments, and, based upon the needs that are seen, assign additional tests that target that particular need. Conversely, over time, it is possible to monitor data for a population of subjects and objectively determine which exercises are most effective for the treatment of certain conditions.

IMC technology not only has the potential to be utilized in an injury screening setting but also in an athletic performance training environment. By use of the technology described herein, the measurement of variables that describe athletic movement can therefore be evaluated in a wide variety of settings, and are no longer limited to sports science facilities.

Performance Assessments

In the same manner that injury screening procedures can be carried out, biomechanical flaws can also be assessed while the subject performs standardized exercises. These assessments serve as a further investigative tool to help determine if the subject is susceptible to future injury.

In summary, the readily accessible testing equipment provided by the IMC technology affords an individual and physician, or the athlete and coach, a wealth of performance measurements to track the progression of the subject during rehabilitation, or an athlete during a training program. The IMC technology is also an accurate and efficient method to assess and compare a large team of athletes.

Table 1 lists some exercises that can be assessed by motion capture technologies along with parameters derivable from the exercises that may form part of relevant motion profile data. It would be understood by one skilled in the art that this is not an exclusive list of exercises. Other exercises and sports moves not listed herein can also be contemplated.

TABLE 1

| Activity | Parameters |
|---|---|
| Balance | Trunk Angle |
| | Trunk deviation from midline |
| | Time to Fail |
| | Hand Counter balance |
| | Adduction angle |
| | Adduction Deviation |
| Double Jump | Vertical distance |
| | Time between landing first jump and take off of second jump |
| Dynamic Skaters | Maximum distance |
| Endurance Skaters | Distance compared to baseline |
| | Time between load positions |
| | Hip-Knee-Ankle Angle at load position |
| | Trunk angle at load position |
| | Adduction at load position |
| Overhead Lunge | Trunk Angle |
| | Hip-Knee-Ankle Angle |
| | Adduction Angle |
| | Knee Displacement |
| Squat series | Difference in head heights |
| | Depth change of the head normalized by subject's height |
| | Hip-Knee-Ankle Angle |
| | Adduction Angle |
| | Knee Displacement |
| | Shoulder difference |
| | Shoulder Hip depth difference |
| | Dorsiflexion |
| Single Leg Dorsiflexion | Dorsiflexion |
| Single Leg Deceleration | Trunk Angle |
| | Trunk deviation from midline |
| | Adduction angle |
| | Adduction deviation |
| Single Leg Squat | Trunk Angle |
| | Hip-Knee-Ankle Angle |
| | Adduction Angle |
| | Knee displacement |
| | Shoulder Hip depth difference |
| Standing Vertical | Vertical in inches. |
| Thoracic Rotation | Shoulder Rotation angle |
| Thoracic mobility | Left Elbow - left shoulder - left hip; Right elbow - right shoulder - right hip |

Certain other constraints may apply. For example, the balance assessment may be comprised of a fixed period of time, say 30 seconds, balanced on each leg in turn. The angle measured when testing for thoracic mobility (or extension) is the one formed by elbow-shoulder-trunk, and is gathered based on depth data readings of each of those points to the image capture device at the end of the movement. For the "Squat" series (which may include overhead squats), data can be normalized based on the angle of the trunk (calculated from depth differences) and the subject's height, i.e., without necessarily relying upon shoulder-hip depth differences. Single leg deceleration is a measure of dynamic stability, specifically hip and trunk stability during a dynamic movement (rather than a static movement like the single leg squat).

As well as movement pathologies, subjects can be measured on performance characteristics such as "eccentric adaptation" and "lower body power". Should an individual fall well below what is appropriate, that person will be trained for these "needs" as well, much like he or she would be trained out of movement pathologies such as poor hip mobility.

Performance assessments can also be sport-specific. Individual sports that lend themselves to this include, but are not limited to: basketball, baseball, soccer, tennis, fencing, and running. Although the same biomechanical measurements may be made as those that are applied to identifying biomechanical pathologies, different parameters, goals, and norms may be utilized. For example, particular sports may demand different ranges of mobility in certain joints than are necessary for everyday life. Furthermore, individuals recorded in the database may be identified as professional or amateur athletes in particular sports, and sport-specific data can therefore be aggregated.

EXAMPLES

Example 0

Use of Microsoft Kinect

An exemplary embodiment of the technology herein utilizes an API (Application Program Interface) to Microsoft's Kinect software in conjunction with a Kinect hardware device. The raw data that is produced by Kinect includes (x,y,z) coordinate data at a sequence of times for the various nodes on a subject's body. Small modifications can be made to the Kinect data such as ensuring that connected nodes for a given individual maintain constant distances between them during the range of the individual's motion. For example, the distance between ankle and knee can vary within the output from Kinect. In this way, data for an individual can be normalized and stored for a session. Other filtering can also be applied to the data to reject spurious measurements, such as where objects in the background of the subject are accidentally recognized by the software and cause the individual's recorded motion to include unnatural poses and ranges of angular variation.

Example 1

Speed Skater

The example movement that will be referenced throughout this rationale to describe the array of measurable performance variables is the speed skater plyometric. This movement has the athlete standing on a single leg, squatting down, and then rapidly performing extension of the ankle, knee and hip to propel himself airborne in a lateral direction and then finishing the sequence by landing on his opposite foot. When this movement is performed in view of the IMC sensors, not only will a variety of performance variables be instantly measured, but an exact animation of the athlete performing the movement will be displayed.

Throughout the assessment of any movement, the angle of each joint is measured. These results are extremely informative, as analysis can be compared to algorithms to determine if the athlete is using the appropriate range of motion of the joint to maximize his ability to develop force. For instance, if an athlete is found to be under-utilizing his hip joint and is not extending the joint far enough, then the athlete will not be fulfilling the potential force production of his hamstrings, or gluteus maximus. Under-utilization may also prompt the athlete to use inefficient compensatory biomechanics in an attempt to yield the same results. For example, a common compensatory method for under-utilization of the hip joint is for the athlete to lean forward and lower their chest towards the ground. This motion not only places extreme stress on the back when the athlete attempts to create rapid force by extending the back, but it also produces an unstable center of mass that is outside of the body. As described previously, measurement of joint angles can also highlight whether the athlete has valgus issues at the knee, while performing jumping and agility movements.

The 'ground angles' that the athlete creates, while performing athletic movements, can also be measured. These angles are those that are made between the surface of the ground (usually a horizontal plane) and the athlete's limb that is in contact with it. This measurement is significant, as it sets the trajectory of the athlete's propulsion if excessive force is applied to the ground. With reference to the speed skater jump, if the ground angle is too large, say around 90°, the athlete will be unable to create significant lateral movement because (s)he doesn't effectively handle forces when moving laterally in deceleration. In acceleration, (or when pushing off the stance leg) a relatively obtuse angle shows poor lateral force generation characteristics. Conversely, if the ground angle is too small, the athlete will be unable to create sufficient elevation to fully extend the ankles, knees and hips during the movement, and may be placing him or herself in a precariously injury prone position. By utilizing the comparison report of the athlete's ground angles to those of the algorithm, the athlete will learn how to maximize his or her performance by applying optimum ground angles when performing agility and plyometric movements.

The athlete's ability to remain stable and controlled while performing athletic movements can also be observed during screening. For instance, during the speed skater plyometric, the ability of the athlete to stabilize while squatting on a single leg and then perform the explosive lateral movement will be assessed. Instability, such as in the trunk, hips, or ankles, may limit the athlete's ability to produce the desired force. If a high degree of instability is observed, the athlete should be provided with a strength training program that will correct this issue. The athlete can then be reevaluated periodically to determine if the prescribed strength-training program is effective or if changes are needed.

By knowing the basic physical data of the athlete such as weight, height and body/mass index, other more universally utilized measures of performance, such as rate of acceleration, velocity and power will be collected by the IMC technology. Measurements of these variables allow for intra/inter subject comparisons, and they can be reassessed subsequently to determine whether the athlete is becoming faster and/or more powerful. Not only will the value of maximum power be measured, but also the athlete's rate of force development. This variable is measured in Newtons per second and is the rate at which force is created by the athlete. The rate of force development will be assessed and shown in both its lateral and vertical planes by the IMC technology. These results are important for the performance assessment of the speed skater plyometric, as results will indicate whether the athlete is applying too much of the total power developed in the vertical plane, therefore creating excessive lift and not performing the lateral movement efficiently.

Example 2

Posture

Posture refers to the orientation of the body's segments and is normally a term used to describe variations of standing and sitting positions. During these static phases, the weight of one of more body segments is being transmitted to the ground or other support surface, where an equal and opposite ground reaction force is being applied to the body. This ground reaction force maintains an equilibrium that allows for the static pose. The size of support surface area has a direct effect on the degree of muscular activation required to maintain the static posture. For example, while in a recumbent position, the muscular activity required to maintain this position is minimal, as there is a large support surface area to distribute the body's weight. By contrast, maintaining a standing upright posture requires a large amount of muscular activation to support the body's alignment, although this is not noticed at the time, unless the period of inactivity is prolonged.

While in a standing posture, the body's weight is transferred distally through the center of the body and is evenly distributed by the feet at ground contact. However, poor posture has been shown to place considerable stress on several regions of the back, most notably the thoracic and lumbar regions. Considerable deviations from normal posture may be aesthetically unpleasant, muscularly inefficient and may predispose individuals to severe injury (Hrysomallis & Goodman, 2001). In fact, it has been concluded that body segments that are out of alignment for extended periods of time will force the muscles supporting the segment to rest in a shortened or lengthened position (Bloomfield, 1994) and, over time, adaptive shortening and lengthening will occur (Novak & Mackinnon, 1997). The characteristic of adaptive shortened muscles are tight and strong, maintaining the opposing muscles in a lengthened and weakened orientation (Kendall et al., 1993). In turn, as these postural deviations are caused by muscular imbalances, they can be identified and altered through targeted training that aims to restore the equilibrium in strength between agonist and antagonist muscles.

Central to posture is the alignment of the vertebral column, as alteration to the alignment of the column will force the body into compensatory actions to stabilize the body. The vertebral column consists of twenty-six bones which are divided into five sections. These regions, from proximal to distal, include the seven cervical vertebrae (neck area), twelve thoracic vertebrae (upper back), five lumbar vertebrae (lower back), and sacral and coccygeal bones (pelvic and tailbone area, respectively).

Example 3

Hip Stability and ACL Injuries

Injuries to the knee account for the highest percentage of injuries sustained to the lower extremities (Powers, 2010). Following an epidemiological survey of injuries in English professional soccer leagues, it was found that 39% of injuries to the knee were ligament sprains/ruptures (Hawkins et al., 2001). Research suggests that many of these injuries, especially those occurring in non-contact situations, may be attributed to abnormal hip mechanics and compensatory biomechanics (Nadler et al., 2000; Leetun et al., 2004; Niemuth et al., 2005).

The proximal end of the femur is situated within the acetebulum of the pelvis, which forms the hip joint. This complex is a ball and socket joint that allows for a high degree of movement. In fact it is the second most mobile joint in the body behind the shoulder (Neumann, 2010). Due to this high degree of mobility, the hip joint is dependent on an advanced set of ligaments, tendons and muscles that are used to stabilize the joint and create force (Powers, 2010). If a segment of this system of soft tissue is not performing efficiently it can render the joint unstable and, as a consequence, alter the athlete's normal biomechanics during movement (Powers, 2010). The knee, the next joint utilized in the chain sequence to produce movement, will then have to perform a compensatory action to correct the inefficient maneuver produced from the hip (Powers, 2010). The knee joint is located at the distal end of the femur and is connected to the tibia through an array of ligaments, tendons and the joint capsule. Due to the tibial condyles being virtually flat and the femoral condyles having a convex shape, the knee joint, from a skeletal point of view, is very unstable (Watkins, 1999). However, this lack of stability is compensated by the support of two menisci, four extracapsular ligaments, and the attached muscles (Watkins, 1999). The menisci are two semilunar shaped disks of fibrocartilage that separate the tibial and femoral condyles (Kent, 2006). Their main purpose is to modify the shape of the articular cartilage to improve the fit between the tibial and femoral bones and to spread the load of forces put on the knee over a wider area to absorb shock (Kent, 2006). The Lateral Collateral Ligament (LCL) attaches superiorly from the lateral epicondyle of the femur to the head of the fibula, and the Medial Collateral Ligament (MCL) attaches from the medial epicondyle of the femur to the medial aspect of the tibia (Watkins, 1999). Within the intercondylar notch, the Anterior Cruciate Ligament (ACL) and the Posterior Cruciate Ligaments (PCL) cross over each other to from an X-shaped configuration that prevents the femur from sliding backward and forward, respectively, thereby preventing the knee from hyperextension (Kent, 2006). The ACL is attached between the posterior aspect of the anterior intercondylar area of the tibial table and the posterior medial aspect of the lateral femoral condyle (Watkins, 1999). The PCL is attached between the posterior aspect of the posterior intercondylar area of the tibial table and the anterior inferior lateral aspect of the medial femoral condyle (Watkins, 1999). Due to the orientation of the menisci and ligaments, the knee joint functions as a hinge joint that allows for flexion and extension as its foremost plane of motion (Watkins, 1999).

During the initial 10% of the gait cycle of walking, the hip joint flexes, adducts and internally rotates (Powers, 2010; Perry, 1992; Simoneau, 2002). The antagonist muscles resisting during these movements are the hip extensors, abductors and external rotators. The resisting forces that these antagonists produce in turn have a stabilizing effect on the joint from producing excessive movement. Weakened hip abductor strength may provide the pathway for excessive hip adduction and internal rotation during weight bearing movements (Powers, 2010). This can cause the knee to shift medially relative to the foot, which is fixed to the ground. As a compensatory action, the tibia is forced to abduct and pronation of the foot occurs. This phenomenon is referred to as knee valgus. The relationship of diminished hip abductor muscle strength to excessive knee valgus has been observed in a number of research studies (Claiborne et al., 2006; Hollman et al., 2009; Jacobs et al., 2007; Wilson et al., 2006).

During weight bearing movements, the contra lateral pelvis may drop during single limb support due to hip abductor muscle weakness (Powers, 2010). This movement in pelvis location causes a shift in the athlete's center of mass away from the supporting leg and, as a result, increases the distance between the ground reaction force (at the location of the foot) and the knee. These events increase the strain on the lateral collateral ligament of the knee and the compressive forces within the medial knee (Powers, 2010). "ACL injuries occur when the external loads placed on the knee exceed that of the tensile strength of the ligament" (Powers, 2010). Therefore, insufficient hip abductor strength, which causes excessive knee valgus, makes an athlete more susceptible to ACL tears, as it increases the strain placed on the ligaments during athletic movements that have a high sum of external force.

Female athletes have been found to be more susceptible to ACL injury than their male counterparts (Arendt & Dick, 1995; Arendt et al., 1999; Harmon & Dick, 1998; Malone et al., 1993; Messina et al., 1999; Prodromos et al., 2007). In a number of studies, they were observed to have greater angles of knee valgus (Chen et al., 2010; Jacobs et al., 2007; Malinzak et al., 2001, McLean et al., 2005; Sigward & Powers, 2006) and that they use less knee and hip flexion when performing athletic movements (Lephart et al., 2002; Malinzak et al., 2001; McLean et al., 2005; Pollard et al., 2007). This is significant, as the strain on the ACL has been found to be greater when external loads are applied to the knee when it is in a position of relative extension, compared to when it is in flexion (Durselen et al., 1995; Markolf et al., 1995).

Following the assessment and comparison of the subject's hip stability and biomechanics during athletic movements to a database of profiles for a population, the subject will be supplied a training intervention to improve their hip stability, if needed. The primary muscles utilized for hip abduction are the gluteus medius and the upper third of the gluteus maximus. Activation of these muscles has been shown to be greatest in exercises that require a significant amount of hip stability, such as single-leg multi-joint movements. The training intervention to strengthen the gluteus medius and gluteus maximus would therefore include movements such as the Bulgarian split squat, a movement that has one of the subject's legs extended to the rear and elevated and the subject single-leg squatting with the leg that is planted on the floor. There are also a variety of other single-leg movements that can be utilized to activate the hip abductor musculature. In addition, more isolated movements, such as the banded clam shell, can be used to improve strength in this area. This movement has the athlete lying on his side with his legs bent at 45° with a rubber band wrapped at knee level around both legs. The athlete proceeds to open a gap between his legs by pivoting at the heel in a movement that resembles the opening of a clamshell. This movement places terrific stress on the gluteus medius and its use over an extended training period will improve hip stability. The subject's progress with this movement can be monitored using the system. For example, if the subject is an injured athlete, comparisons of his or her movements with those in the database, and assessments of the subject's own progress can be used to determine if the subject is ready to return to competition level practice.

Example 4

Combating Hyperkyphosis

Kyphosis is a condition of the thoracic region of the spinal column where a dorsally exaggerated curvature is observed (Kent, 2006). This postural deviation is characterized by a rounded upper back, or in extreme cases, a 'hump-back'. Hyperkyphosis has been attributed to weakness of the spinal extensor musculature (Itoi & Sinaki, 1994). These muscles include the erectar spinae (illiocastalis, longissimus & spinnalis), thoracis, interspinales and the multifides. In fact, training interventions have been shown to significantly decrease the angle of hyperkyphosis for women between the ages of 50-59, over a one year training period (Ball et al., 2009).

If left untreated, the consequences of chronically utilizing a posture with hyperkyphotic characteristics can affect the ability for sufferers to perform a variety of daily activities. For example, it has been reported that women with hyperkyphotic posture have difficulty rising repeatedly from a chair without their arms, have poor balance, slower gait velocity, a wide base for support while standing and decreased velocity when climbing stairs (Balzini et al., 2009, Katzman et al., 2010). Although most of the studies have examined the effects of hyperkyphotic posture on the elderly, it is likely that these factors, such as balance and decreased gait velocity, are observed by hyperkyphotic athletes.

The use of IMC technology to identify cases of slight to extreme hyperkyphosis could be the first step to postural correction. Following the identification that the IMC user (subject) required postural correction, the methods described herein provide a training program, which utilizes these proven methods of thoracic extension, to correct the outstanding deviation. The training intervention would consist of exercises that strengthen the back extensor musculature and those that stretch the anterior thoracic muscles (pectoralis major and minor). These include a variety of weight lifting movements such as rows, the reverse fly, pectoralis major and minor stretches, and prone bridges that target core stability, such as the 'plank'. Following and during the training intervention, the subject will be able to be reliably reassessed for hyperkypotic postural characteristics.

Example 5

Combating Lumbar Hyperlordosis

The natural arch of the lumbar region of the spine is normally convex interiorly and concave posteriorly. The condition of lumbar lordosis refers to an accentuated curvature of this region. Chronic lower back pain has been attributed to lumbar lordosis, as compressive stress is placed on the posterior elements of the lumbar spine (Kent, 2006). This accentuated curvature, while in the erect posture, has been attributed to an anterior tilt of the pelvis, which forces the spine to compensate for this by increasing the curvature of the spine to maintain an erect posture (Kendall and McCreary, 1983).

Research has indicated that the degree of lumbar lordosis is decreased when a posterior pelvic tilt is performed following activation of the abdominal muscles (Day et al., 1984). Further research suggests that anterior pelvic tilt is attributed not only to weak abdominal muscles but also hip extensor muscles (Hrysomallis & Goodman, 2001). The pelvis is further rotated by tight erector spinae and hip flexor muscles (Hrysomallis & Goodman, 2001).

Following an IMC assessment of the lumbar region of the subject's standing posture, a training program is constructed by the methods described herein, if needed, to correct an observed case of lumbar lordosis. Exercises utilized to strengthen abdominal muscles include a variety of stability movements, such as the 'front bridge' and 'bird dog'. The hip extensor musculature will also be targeted for strengthening. The hamstrings and gluteus maximus will be activated in exercises such as the 'Romanian Deadlift', 'Swissball Gluteus Hamstring Hold' and the 'Gluteus & Hamstring Raise', to name a few. Through a variety of stretching movements and yoga poses, such as the 'Warrior 1' and the 'Lying leg crossover stretch', the hip flexors and erector spinae musculature respectively, will be stretched.

Following the training intervention, the subject will be re-assessed to gauge the progress of pre-determined needs, and re-organize the hierarchy of biomechanical issues for the individual.

Example 6

Scapula Stabilization

The shoulder complex plays a pivotal role in upper body force production. This complex, also known as the shoulder girdle, is an incomplete ring of bone proximal to the chest cavity. The manubrium acts as the center piece of the girdle, which is connected to two clavicles that protrude laterally from the manubrium, in either direction. The connection of the manubrium and the clavicle is referred to as the sternoclavicular joint. The lateral end of each clavicle articulates with the acromion process of the corresponding scapula (shoulder blade) to form an acromioclavicular joint. The glenohumeral joint is formed by the articulation of the head of the humerus and the glenoid cavity of the scapula. The humerus binds to the glenohumeral joint capsule by four small muscles; the infraspinatus, subscapularis, supraspinatus and the teres minor. These four muscles are collectively referred to as the rotator cuff and their main purpose is to stabilize shoulder movements by steadying the humeral head in the glenoid cavity (Kent, 2006). As the scapulae are not attached to the axial skeleton, but are in fact held in position at the lateral, superior, posterior aspects of the rib cage by muscles, the shoulder girdle does not complete a full cycle around the body. As a result, the scapulae have considerable range of movement. In fact, this is the second most mobile joint of the body, second only to the hip (Watkins, 1999). The muscles that attach the scapulae to the thorax are the trapezius, levator scapuline, rhomboideus major and minor, serratus anterior and the pectoralis minor. Scapular gliding refers to the ability of the scapula to move in four primary motions. Scapular protraction and retraction refers to the movement of the scapula in an anterior and posterior direction, respectively. Scapula elevation and depression refers to the ability of the scapula to move in a vertical plane superiorly and inferiorly, respectively.

When the shoulder is producing force, the three joints within the shoulder complex, the acromioclavicular, sternoclavicular and the glenohumeral joints, work in a coordinated and a synchronous manner to produce the efficient movement of the upper arm. The role of the scapulae is important because in normal movement the scapula provides a stable base upon which glenohumeral joint motion can occur. This stability depends on the strength and function of the surrounding musculature, the scapula stabilizers. When the muscles are performing efficiently, they dynamically position their glenoid, in relation to the humerus, so that proper glenohumeral mechanics can occur. However, an altered positioning of the glenoid can occur if these muscles are weak and are, in turn, unstable. When improper glenohumeral joint function occurs it can predispose the athlete to shoulder injury and decrease neuromuscular performance. Injuries can be the result of abnormal stress to anterior capsular structures, increased rotator cuff compression and altered biomechanics to compensate for inefficient shoulder mechanics (Voight and Thomson, 2000).

Therefore, strengthening the scapula stabilizing musculature must be an aim of a strength training program for athletes who perform powerful and repeated overhead movements, such as swimmers, baseball players and tennis players. Exercises that engage these muscles include a selection of exercises, both free weight and resistance band tubing based, that result in a degree of scapular retraction, protraction, elevation or depression. Examples of these are rowing motions (which require scapular retraction), pressing movements (producing a scapula protraction motion prior to the eccentric muscle contraction), and shoulder shrugging movements (requiring both scapular elevation and depression).

Utilizing the IMC technology, an athlete's ability to stabilize their scapulae can be examined and assessed through a number of testing protocols. For instance, the path of scapular gliding during such exercises as the push up and pull up, will display whether the athlete is experiencing efficient scapular stabilization qualities from the surrounding musculature.

Example 7

Dorsiflexion Training Regimen

Ankle mobility (dorsiflexion), if inhibited, can impact the body "downstream". Causes of poor dorsiflexion can include, but are not limited to, poor flexibility of the gastroc-soleus complex (calf muscles), prior ankle injuries resulting in scar tissue accumulation around the ankle joint, and aging or abnormal osseous (bone) formation.

Impacts of poor or decreased dorsiflexion on downstream mechanics include: an increase in compensatory pronation through the sub talar and calcaneonavicular joint which in turn can increase internal tibial torsion, a main contributor to valgus of the knee. Another common result of decreased dorsiflexion is excessive hip flexion which places the lumbar spine under undue stress and risk of injury and concurrently can lead to anterior pelvic tilt which itself can impact mechanics throughout the body. Poor hip stability due to a inhibiting of gluteus function, leading to poor contralateral scapula stabilization, and decreased range of motion in the shoulder is another possible complication of poor dorsiflexion.

If a subject's measured dorsiflexion parameters, as detected by IMC technology, fall below established "norms" (based on comparison to published values or a relevant population), the subject will be provided a training regimen that includes ankle mobility exercises designed to: 1) Inhibit and lengthen overactive or tight structures that are restricting dorsiflexion, 2) Mobilize the affected joints, 3) Strengthen and stabilize supporting structures and muscles responsible for initiating dorsiflexion, and 4) Implement and train dorsiflexion in functional/dynamic movements. An example of this would be, set forth in Table 2:

TABLE 2

| Action | Comments |
|---|---|
| Inhibit/Rollout Calf: 45-60 seconds left and right; Hamstring: 45-60 seconds left and right; | Place strap above ankle joint line Keep heel flat on ground Push knee over foot |
| Strap Mobilization (2 × 10 L + R): "Down Dog" Calf: 2 × 30 seconds left and right; Step Stretch (Drop heel off step): 2 × 30 seconds left and right; Straight Leg Raise (2 × 30 left and right): | Place strap around foot Find stretch in hamstring Push toe into strap and return to stretch 10× |
| Balance + Active dorsiflexion (2 × 30 s left and right) | Balance on 1 leg Flex toes up & down during balance |
| Heel Raise (2 up 1 down) (2 × 10 left and right): | Standing on step (hold on) Raise heels using 2 feet Lower heel on 1 foot |
| Squat + Reach (2 × 8 left and right) | Balancing on 1 leg Squat to end range keeping heel on ground Reach dumbbell across body |
| Wall Sit + Angle (3 × 30 seconds) | Squatting against wall (knees inline with feet); Lift toes off floor; Raise arms above head; Keep elbows on wall; Repeat; |
| Dowel Hop (3 × 30 sec) | 2 legs Jump side to side over line Keep toes up landing on balls of feet |

LIST OF REFERENCES

Arendt, E., Dick, R., Knee injury patterns among men and women in collegiate basketball and soccer. NCAA data and review of literature. Am J Sports Med. 1995; 23:694-701.

Arendt, E. A., Agel, J., Dick, R., Anterior Cruciate Ligament Injury Patterns Among Collegiate Men and Women. *J Athl Train.* 1999; 34:86-92.

Ball, J. M., Cagle, P., Johnson, B. E., Lucasey, C., Lukert, B. P., Spinal extension exercises prevent natural kyphosis. *Osteoporos int.* 2009; 20: 481-489.

Balzini, L., Vannucchi, L., Benvenuti, F., et al., Clinical characteristics of flexed posture in elderly women. J Am Geriatr Soc 2003; 51:1419-1426. [PubMed: 14511162]

Bloomfield, J., Postural considerations in sport performance. In: *Applied Anatomy and Biomechanics in Sport*. J. Bloomfield, T. R. Ackland, and B. C. Elliot, eds. Melbourne: Blackwell Scientific Publication, 1994. pp. 95-109.

Chen, Y. J., Scher, I., Powers, C. M., Quantification of patellofemoral joint reaction forces during functional tasks: a subject specific, three dimensional model. J. Appl. Biomech. 2010; In press.

Claiborne, T. L., Armstrong, C. W., Gandhi, V., Pincivero, D. M., Relationship between hip and knee strength and knee valgus during a single leg squat. J. Appl. Biomech. 2006; 22:41-50.

Day, J. W., Smidt, G. L., Lehmann, T., Effect of pelvic tilt on standing posture. *Phys The,* 64:510-516, 1984

Durselen, L., Claes, L., Kiefer, H., The influence of muscle forces and external loads on cruciate ligament strain. Am. J. Sports Med., 1995; 23:129-136.

Harmon, K. G., Dick, R., The relationship of skill level to anterior cruciate ligament injury. Clin. J. Sport Med. 1998; 8:260-265.

Hawkins, R. D., Hulse, M. A., Wilkinson, C., Hodson, A., Gibson, M. The association football medical research programme: an audit of injuries in professional football. *British Journal of Sports Medicine.* 2001; 35:43-47

Hollman J. H., Ginos, B. E., Kozuchowski, J., Vaughn, A. S., Krause, D. A., Youdas, J. W., Relationships between knee valgus, hip-muscle strength, and hip-muscle recruitment during a single-limb step-down. *J Sport Rehabil.* 2009; 18:104-117.

Hrysomallis, C., Goodman, C., (2001). A review of resistance exercise and posture realignment. *Journal of Strength and Conditioning Research,* 15(3), 385-390.

Itoi, E., and Sinaki, M., Effect of back strengthening exercise on posture in healthy women 49 to 65 years of age. *Mayo Clin. Proc.* 69:1054-1059.1994.

Jacobs, C. A., Uhl, T. L., Mattacola, C. G., Shapiro, R., Rayens, W. S., Hip abductor function and lower extremity landing kinematics: sex differences. *J. Athl. Train.* 2007; 42:76-83.

Katzman, W. B., Sellmeyer, D. E., Stewart, A. L., Wanek, L., Hamel, K. A., Changes in flexed posture, musculoskeletal impairments, and physical performance after group exercise in communitydwelling older women. Arch. Phys. Med. Rehabil. 2007; 88:192-199.

Kendall, F. P., McCreary, E. K., *Muscles Testing and Function* (3rd ed.). Baltimore: Williams & Wilkins, 1983.

Kendall, F. P., McCreary, E. K., and Provance, P. G., *Muscles Testing and Function* (4th ed.). Baltimore: Williams & Wilkins, 1993. pp. 27-176.

Kent, M., Oxford Dictionary of Sports Sciences and Medicine. Oxford Publishing, 2006

Leetun, D. T., Ireland, M. L., Willson, J. D., Ballantyne, B. T., Davis, I. M., Core stability measures as risk factors for lower extremity injury in athletes. *Med Sci Sports Exerc.* 2004; 36:926-934.

Lephart, S. M., Ferris, C. M., Riemann, B. L., Myers, J. B., Fu, F. H., Gender differences in strength and lower extremity kinematics during landing. *Clin Orthop Relat Res.* 2002; 162-169.

Malinzak, R. A., Colby, S. M., Kirkendall, D. T., Yu, B., Garrett, W. E. A., Comparison of knee joint motion patterns between men and women in selected athletic tasks. *Clin Biomech (Bristol, Avon).* 2001; 16:438-445.

Malone, T. R., Hardaker, W. T., Garrett, W. E., Feagin, J. A., Bassett, F. H., Relationship of gender to ACL injuries in intercollegiate basketball players. *J South Orthop Assoc.* 1993; 2:694-701.

Markolf, K. L., Burchfield, D. M., Shapiro, M. M., Shepard, M. F., Finerman, G. A., Slauterbeck, J. L., Combined knee loading states that generate high anterior cruciate ligament forces. *J Orthop Res.* 1995; 13:930-935.

McLean, S. G., Walker, K. B., van den Bogert, A. J., Effect of gender on lower extremity kinematics during rapid direction changes: an integrated analysis of three sports movements. *J Sci Med Sport,* 2005; 8:411-422.

Messina, D. F., Farney, W. C., DeLee, J. C., The incidence of injury in Texas high school basketball. A prospective study among male and female athletes. *Am J Sports Med.* 1999; 27:294-299.

Nadler, S. F., Malanga, G. A., DePrince, M., Stitik, T. P., Feinberg, J. H., The relationship between lower extremity injury, low back pain, and hip muscle strength in male and female collegiate athletes. *Clin J Sport Med.,* 2000; 10:89-97.

Neumann D A. Kinesiology of the hip: a focus on muscular actions. *J Orthop Sports Phys Ther.* 2010; 40:82-94. dx.doi.org/doi:10.2519/jospt.2010.3025

Neumann D A. *Kinesiology of the Musculoskeletal System*. St Louis, Mo.: Mosby Inc; 2002.

Niemuth, P. E., Johnson, R. J., Myers, M. J., Thieman, T. J., Hip muscle weakness and overuse injuries in recreational runners. *Clin J Sport Med.* 2005; 15:14-21.

Novak, C. B., and MacKinnon, S. E., Repetitive use and static postures: a source of nerve compression and pain. *J. Hand Ther.* 10:151-159. 1997.

Perry, J. *Gait Analysis: Normal and Pathological Function*, Thorofare, N.J.: Slack Inc; 1992.

Pollard, C. D., Sigward, S. M., Powers, C. M. Gender differences in hip joint kinematics and kinetics during side-step cutting maneuver. *Clin J Sport Med.* 2007; 17:38-42.

Powers, C. M., The influence of Abnormal Hip Mechanics on Knee Injury: A biomechanical Perspective. *Journal of orthopaedic & Sports Physical Therapy.* 2010: 40:2

Prodromos, C. C., Han, Y., Rogowski, J., Joyce, B., Shi, K., A meta-analysis of the incidence of anterior cruciate ligament tears as a function of gender, sport, and a knee injury-reduction regimen. *Arthroscopy.* 2007; 23:1320-1325 e1326.

Sigward, S. M., Powers, C. M., The influence of gender on knee kinematics, kinetics and muscle activation patterns during side-step cutting. *Clin Biomech (Bristol, Avon).* 2006; 21:41-48. Online at: dx.doi.org/10.1016/j.clinbiomech.2005.08.001

Simoneau, G. Kinesiology of walking. In: Neumann, D. A., eds. *Kinesiology of the Musculoskeletal System*. St Louis, Mo.: Mosby Inc; 2002:523-569.

Voight, M. L., and Thomson, B. C., (2000): The role of the scapula in the rehabilitation of shoulder injuries. *Journal of Athletic Training* 35: 364-372.

Watkins, J., Structure and Function of the Musculoskeletal System. UK: Human Kinetics Publishing. (1998).

Willson, J. D., Ireland, M. L., Davis, I. Core strength and lower extremity alignment during single leg squats. *Med Sci Sports Exerc.* 2006; 38:945-952. Online at: dx.doi.org/10.1249/01.mss.0000218140.05074.fa All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:

1. A computer-based method for identifying a training regimen for a subject, the method performed on at least one computer having a processor, a memory and input/output capability, the method comprising:
   recording, via infrared motion capture technology that comprises a single sensor that recognizes one or more nodes at various positions on the subject's anatomy, three-dimensional (x,y,z) coordinates of the one or more nodes at a sequence of times, t, while the subject performs one or more exercises;
   constructing, by a first computer, a motion profile for the subject based on a sequence of the three-dimensional (x,y,z) coordinates of the one or more nodes at the sequence of times, t, wherein the motion profile comprises a range of node angle values identified between at least two or more nodes while the subject performs the one or more of the exercises;
   comparing, by the first computer, the motion profile of the subject with a database of previously recorded motion profiles from a statistical sampling of motion profiles of a population of subjects, the statistical sampling of motion profiles of the population selected based on a demographic corresponding to the subject;
   identifying one or more restricted ranges of motion or combination of motions based on a deviation between the motion profile for the subject and the previously recorded motion profiles from the statistical sampling of motion profiles of the population of subjects in the database;
   generating, by the first computer, a scoring function for a biomechanical aspect of a movement pathology based on the statistical sampling of motion profiles of the population of subjects performing the one or more exercises;
   determining, by the first computer, a score for the motion profile of the subject using the scoring function and at least one biomechanical value corresponding to the subject performing the one or more recorded exercises; and
   communicating, via an output device, a training regimen for the subject, the training regimen developed based on the score for the motion profile of the subject.

2. The method of claim 1, wherein each node is selected from the group consisting of: left and right elbow, left and right wrist, left and right hand, left and right shoulder, left and right knee, left and right ankle, left and right hip, head, neck, center of hips, center of shoulders, left and right foot, and lower-back.

3. The method of claim 1, wherein the training regimen is designed to alleviate the one or more restricted ranges of motion or combinations of motion arising from an injury or physical abnormality.

4. The method of claim 1, wherein the training regimen comprises one or more exercises selected from a set of exercises stored in a second database.

5. The method of claim 1, wherein the score indicates whether the restricted range of motion or combination of motions arising from an injury or physical abnormality is present for that motion profile.

6. The method of claim 1, wherein the sequence of times includes 30 measurements per second over a period of 1-2 minutes.

7. The method of claim 1, wherein the database stores motion profiles for the subject, recorded at various times.

8. The method of claim 1, wherein:
   the recording the one or more exercises of the subject takes place at a first location;
   a second computer is situated at a second location; and
   the recorded one or more exercises are transmitted to the second computer.

9. The method of claim 8, wherein the output device is at the first location.

10. The method of claim 1, further comprising receiving, by the first computer, from a second computer, previously recorded motion profiles of the population of subjects from the database of previously recorded motion profiles, wherein the database is stored on the second computer.

11. The method of claim 1, wherein the exercises are selected from: balance, double jump, dynamic skaters, endurance skaters, overhead lunge, single leg dorsiflexion, single leg squat, standing vertical, thoracic rotation, thoracic extension and overhead squat series.

12. The method of claim 1, wherein the restricted range of motion or combination of motions arising from an injury or physical abnormality is selected from: dorsiflexion, hip stability, hip mobility, trunk stability, thoracic mobility, thoracic rotation, lumbar lordosis, and varus or valgus deformations.

13. The method of claim 1, further comprising, comparing the motion profile of the subject with an average motion profile determined from the database of previously recorded motion profiles.

14. The method of claim 1, wherein the demographic corresponding to the subject includes at least one of gender, body mass index, sport, type of activity, activity level, or age.

15. An apparatus for identifying a training regimen for a subject, the apparatus comprising:
   a single infrared recording device that is not worn by the subject and which recognizes one or more nodes at various positions on the subject's anatomy, and which receives data that describes three-dimensional (x,y,z) coordinates of the one or more nodes at a sequence of times, t, while the subject performs one or more exercises;
   a transmission channel for communicating the data to one or more computing devices;
   wherein the one or more computing devices each comprises a memory, an output device, and one or more processors configured with instructions to:
      construct a motion profile for the subject based on a sequence of the three-dimensional (x,y,z) coordinates of the one or more nodes at the sequence of times, t, wherein the motion profile comprises a range of joint angle values identified between at least two or more nodes while the subject performs the one or more exercises;
      compare the motion profile of the subject with a database of previously recorded motion profiles from a statistical sampling of motion profiles of a population of subjects, the statistical sampling of motion profiles of the population selected based on a demographic corresponding to the subject, wherein the database is stored in one of the memories;
      identify a restricted range of motion or combination of motions based on a deviation between the motion profile for the subject and the previously recorded motion profiles from the statistical sampling of motion profiles of the population of subjects in the database;

generate a scoring function for a biomechanical aspect of a movement pathology based on the statistical sampling of motion profiles of the population of subjects performing the one or more exercises;

determine a score for the motion profile of the subject using the scoring function and at least one biomechanical value corresponding to the subject performing the one or more recorded exercises; and communicate, via the output device, a training regimen for the subject, the training regimen developed based on the score for the motion profile of the subject.

16. The apparatus of claim 15, wherein the training regimen is designed to alleviate the restricted range of motion or combination of motions arising from an injury or physical abnormality.

17. The apparatus of claim 15, wherein the score indicates whether the restricted range of motion or combination of motions arising from an injury or physical abnormality is present for that motion profile.

18. The apparatus of claim 15, wherein each node is selected from the group consisting of: left and right elbow, left and right wrist, left and right hand, left and right shoulder, left and right knee, left and right ankle, left and right hip, head, neck, center of hips, center of shoulders, left and right foot, and lower-back.

* * * * *